(12) United States Patent
Duvert et al.

(10) Patent No.: US 8,586,628 B2
(45) Date of Patent: Nov. 19, 2013

(54) USE OF PROPINEB AS BIRD REPELLENT

(75) Inventors: Patrice Duvert, Lyons (FR); Ralf Barfknecht, Cologne (DE)

(73) Assignee: Bayer Cropscience AG, Monheim (DE)

( * ) Notice: Subject to any disclaimer, the term of this patent is extended or adjusted under 35 U.S.C. 154(b) by 22 days.

(21) Appl. No.: 13/182,325

(22) Filed: Jul. 13, 2011

(65) Prior Publication Data

US 2011/0269832 A1    Nov. 3, 2011

Related U.S. Application Data

(62) Division of application No. 12/762,872, filed on Apr. 19, 2010, now abandoned.

(30) Foreign Application Priority Data

Apr. 22, 2009  (EP) .................................. 09158471

(51) Int. Cl.
- *A01N 47/10* (2006.01)
- *A01N 25/00* (2006.01)
- *A01N 25/26* (2006.01)

(52) U.S. Cl.
USPC ............................ 514/479; 424/405; 504/100

(58) Field of Classification Search
USPC ............................ 514/479; 424/405; 504/100
See application file for complete search history.

(56) References Cited

U.S. PATENT DOCUMENTS

| | | | |
|---|---|---|---|
| 4,639,266 A | 1/1987 | Heubach et al. | |
| 4,785,105 A | 11/1988 | Hubele | |
| 4,881,966 A | 11/1989 | Nyffeler et al. | |
| 4,891,057 A | 1/1990 | Sohn et al. | |
| 4,902,340 A | 2/1990 | Hubele | |
| 4,937,261 A | 6/1990 | Wilde | |
| 4,944,790 A | 7/1990 | Moser et al. | |
| 5,314,863 A | 5/1994 | Loeher et al. | |
| 5,380,852 A | 1/1995 | Schuetze et al. | |
| 5,516,750 A | 5/1996 | Willms et al. | |
| 5,950,360 A * | 9/1999 | Heinrich et al. | ............ 47/58.1 R |
| 6,071,856 A | 6/2000 | Baker et al. | |
| 6,228,885 B1 | 5/2001 | Palla et al. | |
| 6,235,680 B1 | 5/2001 | Ziemer et al. | |
| 6,251,827 B1 | 6/2001 | Ziemer et al. | |
| 6,294,504 B1 | 9/2001 | Tobler et al. | |
| 7,838,463 B2 | 11/2010 | Bickers et al. | |
| 2004/0224844 A1 | 11/2004 | Bickers et al. | |
| 2007/0299264 A1 | 12/2007 | Huang et al. | |
| 2009/0170938 A1 * | 7/2009 | Hauser-Hahn et al. | ....... 514/539 |

FOREIGN PATENT DOCUMENTS

| | | |
|---|---|---|
| DE | 1020057837 A1 * | 6/2007 |
| EP | 0 086 750 | 8/1983 |
| EP | 0 094 349 | 11/1983 |
| EP | 0 174 562 | 3/1986 |
| EP | 0 191 736 | 8/1986 |
| EP | 0 268 554 | 5/1988 |
| EP | 0 346 620 | 12/1989 |
| EP | 0 365 484 | 4/1990 |
| EP | 0 492 366 | 7/1992 |
| EP | 0 582 198 | 2/1994 |
| WO | 91/07874 | 6/1991 |
| WO | 91/08202 | 6/1991 |
| WO | 95/07897 | 3/1995 |
| WO | 97/45016 | 12/1997 |
| WO | 98/13361 | 4/1998 |
| WO | 98/38856 | 9/1998 |
| WO | 99/00020 | 1/1999 |
| WO | 99/16744 | 4/1999 |
| WO | 02/34048 | 5/2002 |
| WO | 2004/084631 | 10/2004 |
| WO | 2005/016001 | 2/2005 |
| WO | 2007/023719 | 3/2007 |
| WO | 2007/023764 | 3/2007 |
| WO | 2007/149134 | 12/2007 |

* cited by examiner

*Primary Examiner* — Benjamin Packard
(74) *Attorney, Agent, or Firm* — Miles & Stockbridge P.C.

(57) ABSTRACT

The present invention relates to the novel use of Propineb as bird repellent.

20 Claims, No Drawings

USE OF PROPINEB AS BIRD REPELLENT

CROSS REFERENCE TO RELATED APPLICATION

This application is a Divisional of U.S. application Ser. No. 12/762,872, filed Apr. 19, 2010, which claims priority to European application no. 09158471.4, filed Apr. 22, 2009, the content of which is incorporated herein by reference in its entirety.

BACKGROUND OF THE INVENTION

1. Field of the Invention

The present invention relates to the novel use of Propineb as bird repellent.

2. Description of Related Art

To avoid, after application, plant treatment agents present in solid form or seeds, undressed or dressed with agrochemically active compounds, being eaten by birds, it is frequently necessary to use substances having bird-repellent properties. Anthraquinone is known as a substance having such a bird repellent action (cf. Farm Chemicals Handbook '99, C27), but Anthraquinone is not registered anymore in Europe (therefore, not anymore a product available for cereals). However, it is disadvantageous that the activity of this substance at low application rates is not always sufficient. Furthermore, dithiocarbamates like Thiram and Ziram are also know as bird repellents (cf. The Pesticide Manual, 11$^{th}$ Edition 1997, pages 1277-1279, *J. Forestry* 1962, 60, 37-39, and *FAO Plant Protection Bull.* 1960, 8, 38-42).

Furthermore, it is known that Propineb has fungicidal properties and can be used for controlling various plant diseases (cf. The Pesticide Manual, 11$^{th}$ Edition 1997, pages 1032-1034 and GB Patent 935,981). Propineb is a bis-dithiocarbamate and thus has some similarities with dithiocarbamates (e.g. both classes are multi-site fungicides). But there are also differences in their fungicide spectrum. The bis-dithiocarbamates are generally superior against downy mildew, late blight diseases whereas dithiocarbamates are superior against ascomycetes diseases. Also, Thiram is recognized as a good anti-Pythium control. Bis-dithiocarbamates are generally weaker against this pathogen.

SUMMARY OF THE INVENTION

Surprisingly, it has now been found that Propineb of the formula (I)

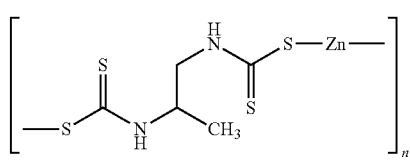

is highly suitable for use as bird repellent.

It is extremely surprising that Propineb can be used for protecting seeds or plant treatment agents against bird feeding, since such properties have hitherto been unknown of this substance.

DETAILED DESCRIPTION OF A PREFERRED EMBODIMENT

Propineb which can be used according to the invention can be employed as such or in the form of customary formulations, such as solutions, emulsions, suspensions, powders, pastes, etc. Application is then carried out by customary methods. Thus, for example, it is possible to dress seeds with preparations comprising the active compounds of the formula (I), if appropriate in a mixture with other agrochemically active compounds and customary additives. A further type of application comprises mixing substances which can be used according to the invention either as such or in formulated form with other agrochemically active compounds and with customary formulation auxiliaries and preparing solid plant treatment agents, such as granules or baits, from these preparations.

Accordingly, the present invention also relates to bird-repellent agrochemical compositions comprising A) Propineb B) at least one agrochemically active compound, in addition to extenders and/or surfactants.

In the present context, agrochemically active compounds are to be understood as meaning all substances which are customarily used for treating plants. Fungicides, bactericides, insecticides, acaricides, nematicides, molluscicides, safeners, plant growth regulators and plant nutrients may be mentioned as being preferred.

Examples of fungicides which may be mentioned are:

(1) Inhibitors of the nucleic acid synthesis, for example benalaxyl, benalaxyl-M, bupirimate, clozylacon, dimethirimol, ethirimol, furalaxyl, hymexazol, metalaxyl, metalaxyl-M, ofurace, oxadixyl and oxolinic acid.

(2) Inhibitors of the mitosis and cell division, for example benomyl, carbendazim, chlorfenazole, diethofencarb, ethaboxam, fuberidazole, pencycuron, thiabendazole, thiophanate, thiophanate-methyl and zoxamide.

(3) Inhibitors of the respiration, for example diflumetorim as CI-respiration inhibitor; bixafen, boscalid, carboxin, fenfuram, flutolanil, fluopyram, furametpyr, furmecyclox, isopyrazam (9R-component), isopyrazam (9S-component), mepronil, oxycarboxin, penthiopyrad, thifluzamide as CII-respiration inhibitor; amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyribencarb, trifloxystrobin as CIII-respiration inhibitor.

(4) Compounds capable to act as an uncoupler, like for example binapacryl, dinocap, fluazinam and meptyldinocap.

(5) Inhibitors of the ATP production, for example fentin acetate, fentin chloride, fentin hydroxide, and silthiofam.

(6) Inhibitors of the amino acid and/or protein biosynthesis, for example andoprim, blasticidin-S, cyprodinil, kasugamycin, kasugamycin hydrochloride hydrate, mepanipyrim and pyrimethanil.

(7) Inhibitors of the signal transduction, for example fenpiclonil, fludioxonil and quinoxyfen.

(8) Inhibitors of the lipid and membrane synthesis, for example biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl and vinclozolin.

(9) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, viniconazole and voriconazole.

(10) Inhibitors of the cell wall synthesis, for example benthiavalicarb, dimethomorph, flumorph, iprovalicarb, mandipropamid, polyoxins, polyoxorim, prothiocarb, validamycin A, and valiphenal.

(11) Inhibitors of the melanine biosynthesis, for example carpropamid, diclocymet, fenoxanil, phthalide, pyroquilon and tricyclazole.

(12) Compounds capable to induce a host defense, like for example acibenzolar-S-methyl, probenazole, and tiadinil.

(13) Compounds capable to have a multisite action, like for example bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, sulphur and sulphur preparations including calcium polysulphide, thiram, tolylfluanid, zineb and ziram.

(14) Further compounds like for example 2,3-dibutyl-6-chlorothieno[2,3-d]pyrimidin-4(3H)-one, ethyl (2Z)-3-amino-2-cyano-3-phenylprop-2-enoate, N-[2-(1,3-dimethylbutyl)phenyl]-5-fluoro-1,3-dimethyl-1H-pyrazole-4-carboxamide, N-{2-[1,1'-bi(cyclopropyl)-2-yl]phenyl}-3-(difluoromethyl)-1-methyl-1H-pyrazole-4-carboxamide, 3-(difluoromethyl)-1-methyl-N-(3',4',5'-trifluorobiphenyl-2-yl)-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, (2E)-2-(2-{[6-(3-chloro-2-methylphenoxy)-5-fluoropyrimidin-4-yl]oxy}phenyl)-2-(methoxyimino)-N-methylethanamide, (2E)-2-{2-[({[(2E,3E)-4-(2,6-dichlorophenyl)but-3-en-2-ylidene]amino}-oxy)methyl]phenyl}-2-(methoxyimino)-N-methylethanamide, 2-chloro-N-(1,1,3-trimethyl-2,3-dihydro-1H-inden-4-yl)pyridine-3-carboxamide, N-(3-ethyl-3,5,5-trimethylcyclohexyl)-3-(formylamino)-2-hydroxybenzamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)-ethylidene]amino}oxy)methyl]phenyl}-2-(methoxyimino)-N-methylethanamide, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N-ethyl-N-methyl-N'-{2-methyl-5-(trifluoromethyl)-4-[3-(trimethylsilyl)propoxy]phenyl}imidoformamide, N'-{5-(difluoromethyl)-2-methyl-4-[3-(trimethylsilyl)propoxy]phenyl}-N-ethyl-N-methylimidoformamide, Sedaxane, O-{1-[(4-methoxyphenoxy)methyl]-2,2-dimethylpropyl} 1H-imidazole-1-carbothioate, N-[2-(4-{[3-(4-chlorophenyl)prop-2-yn-1-yl]oxy}-3-methoxyphenyl)ethyl]-N²-(methylsulfonyl)valinamide, 5-chloro-7-(4-methylpiperidin-1-yl)-6-(2,4,6-trifluorophenyl)[1,2,4]triazolo[1,5-a]pyrimidine, 5-amino-1,3,4-thiadiazole-2-thiol, propamocarbfosetyl, 1-[(4-methoxyphenoxy)methyl]-2,2-dimethylpropyl 1H-imidazole-1-carboxylate, 1-methyl-N-[2-(1,1,2,2-tetrafluoroethoxy)phenyl]-3-(trifluoromethyl)-1H-pyrazole-4-carboxamide, 2,3,5,6-tetrachloro-4-(methylsulfonyl)pyridine, 2-butoxy-6-iodo-3-propyl-4H-chromen-4-one, 2-phenylphenol and salts, 3-(difluoromethyl)-1-methyl-N-[2-(1,1,2,2-tetrafluoroethoxy)phenyl]-1H-pyrazole-4-carboxamide, 3,4,5-trichloropyridine-2,6-dicarbonitrile, 3-5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, quinolin-8-ol, quinolin-8-ol sulfate (2:1) (salt), 5-methyl-6-octyl-3,7-dihydro[1,2,4]triazolo[1,5-a]pyrimidin-7-amine, 5-ethyl-6-octyl-3,7-dihydro[1,2,4]triazolo[1,5-a]pyrimidin-7-amine, benthiazole, bethoxazin, capsimycin, carvone, chinomethionat, chloroneb, cufraneb, cyflufenamid, cymoxanil, cyprosulfamide, dazomet, debacarb, dichlorophen, diclomezine, dicloran, difenzoquat, difenzoquat methylsulphate, diphenylamine, ecomate, ferimzone, flumetover, fluopicolide, fluoroimide, flusulfamide, flutianil, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio)methyl]phenyl}-3-methoxyacrylate, methyl isothiocyanate, metrafenone, (5-bromo-2-methoxy-4-methylpyridin-3-yl)(2,3,4-trimethoxy-6-methylphenyl)methanone, mildiomycin, tolnifanide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(Z)-[(cyclopropylmethoxy)imino][6-(difluoromethoxy)-2,3-difluorophenyl]methyl}-2-phenylacetamide, N-{(E)-[(cyclopropylmethoxy)imino][6-(difluoromethoxy)-2,3-difluorophenyl]methyl}-2-phenylacetamide, natamycin, nickel dimethyldithiocarbamate, nitrothal-isopropyl, octhilinone, oxamocarb, oxyfenthiin, pentachlorophenol and salts, phenazine-1-carboxylic acid, phenothrin, phosphorous acid and its salts, propamocarb fosetylate, propanosine-sodium, proquinazid, pyrrolnitrine, quintozene, S-prop-2-en-1-yl 5-amino-2-(1-methylethyl)-4-(2-methylphenyl)-3-oxo-2,3-dihydro-1H-pyrazole-1-carbothioate, tecloftalam, tecnazene, triazoxide, trichlamide, 5-chloro-N'-phenyl-N'-prop-2-yn-1-ylthiophene-2-sulfonohydrazide and zarilamid.

Examples of bactericides which may be mentioned are: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Examples of insecticides, acaricides and nematicides which may be mentioned are:

(1) Acetylcholinesterase (AChE) inhibitors, for example carbamates, e.g. alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, and xylylcarb; or organophosphates, e.g. acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl, O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion, and imicyafos.

(2) GABA-gated chloride channel antagonists, for example organochlorines, e.g. camphechlor, chlordane, endosulfan, gamma-HCH, HCH, heptachlor, lindane, and methoxy-chlor; or fiproles (phenylpyrazoles), e.g. acetoprole, ethiprole, fipronil, pyrafluprole, pyriprole, and vaniliprole.

(3) Sodium channel modulators/voltage-dependent sodium channel blockers, for example pyrethroids, e.g. acrinathrin, allethrin (d-cis-trans, d-trans), beta-cyfluthrin, bifenthrin, bioallethrin, bioallethrin S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R trans isomer), prallethrin, profluthrin, protrifenbute, pyresmethrin, resmethrin, RU 15525, silafluofen, tau-fluvalinate, tefluthrin, terallethrin, tetramethrin (-1R-isomer), tralomethrin, transfluthrin, ZXI 8901, pyrethrin (pyrethrum), eflusilanat; DDT; or methoxychlor.

(4) Nicotinergic acetylcholine receptor agonists/antagonists, for example chloronicotinyls, e.g. acetamiprid, clothianidin, dinotefuran, imidacloprid, imidaclothiz, nitenpyram, nithiazine, thiacloprid, thiamethoxam, AKD-1022; or nicotine, bensultap, cartap, thiosultap-sodium, and thiocylam.

(5) Allosteric acetylcholine receptor modulators (agonists), for example spinosyns, e.g. spinosad and spinetoram.

(6) Chloride channel activators, for example mectins/macrolides, e.g. abamectin, emamectin, emamectin benzoate, ivermectin, lepimectin, and milbemectin; or juvenile hormone analogues, e.g. hydroprene, kinoprene, methoprene, epofenonane, triprene, fenoxycarb, pyriproxifen, and diofenolan.

(7) Active ingredients with unknown or non-specific mechanisms of action, for example gassing agents, e.g. methyl bromide, chloropicrin and sulfuryl fluoride; selective antifeedants, e.g. cryolite, pymetrozine, pyrifluquinazon and flonicamid; or mite growth inhibitors, e.g. clofentezine, hexythiazox, etoxazole.

(8) Oxidative phosphorylation inhibitors, ATP disruptors, for example diafenthiuron; organotin compounds, e.g. azocyclotin, cyhexatin and fenbutatin oxide; or propargite, tetradifon.

(9) Oxidative phoshorylation decouplers acting by interrupting the H proton gradient, for example chlorfenapyr, binapacryl, dinobuton, dinocap and DNOC.

(10) Microbial disruptors of the insect gut membrane, for example Bacillus thuringiensis strains.

(11) Chitin biosynthesis inhibitors, for example benzoylureas, e.g. bistrifluron, chlorfluazuron, diflubenzuron, fluazuron, flucycloxuron, flufenoxuron, hexaflumuron, lufenuron, novaluron, noviflumuron, penfluoron, teflubenzuron or triflumuron.

(12) Buprofezin.

(13) Moulting disruptors, for example cyromazine.

(14) Ecdysone agonists/disruptors, for example diacylhydrazines, e.g. chromafenozide, halofenozide, methoxyfenozide, tebufenozide, and Fufenozide (JS118); or azadirachtin.

(15) Octopaminergic agonists, for example amitraz.

(16) Site III electron transport inhibitors/site II electron transport inhibitors, for example hydramethylnon; acequinocyl; fluacrypyrim; or cyflumetofen and cyenopyrafen.

(17) Electron transport inhibitors, for example Site I electron transport inhibitors, from the group of the METI acaricides, e.g. fenazaquin, fenpyroximate, pyrimidifen, pyridaben, tebufenpyrad, tolfenpyrad, and rotenone; or voltage-dependent sodium channel blockers, e.g. indoxacarb and metaflumizone.

(18) Fatty acid biosynthesis inhibitors, for example tetronic acid derivatives, e.g. spirodiclofen and spiromesifen; or tetramic acid derivatives, e.g. spirotetramat.

(19) Neuronal inhibitors with unknown mechanism of action, e.g. bifenazate.

(20) Ryanodine receptor effectors, for example diamides, e.g. flubendiamide, (R),(S)-3-chloro-$N^1$-{2-methyl-4-[1,2,2,2-tetrafluoro-1-(trifluoromethyl)ethyl]phenyl}-$N^2$-(1-methyl-2-methylsulphonylethyl)phthalamide, chlorantraniliprole (Rynaxypyr), or Cyantraniliprole (Cyazypyr).

(21) Further active ingredients with unknown mechanism of action, for example amidoflumet, benclothiaz, benzoximate, bromopropylate, buprofezin, chinomethionat, chlordimeform, chlorobenzilate, clothiazoben, cyclopene, dicofol, dicyclanil, fenoxacrim, fentrifanil, flubenzimine, flufenerim, flutenzin, gossyplure, japonilure, metoxadiazone, petroleum, potassium oleate, pyridalyl, sulfluramid, tetrasul, triarathene or verbutine; or one of the following known active compounds 4-{[(6-bromopyrid-3-yl)methyl](2-fluoroethyl)amino}furan-2(5H)-one, 4-{[(6-fluoropyrid-3-yl)methyl](2,2-difluoroethyl)amino}furan-2(5H)-one, 4-{[(2-chloro-1,3-thiazol-5-yl)methyl](2-fluoroethyl)amino}furan-2(5H)-one, 4-{[(6-chloropyrid-3-yl)methyl](2-fluoroethyl)amino}furan-2(5H)-one, 4-{[(6-chloropyrid-3-yl)methyl](2,2-difluoroethyl)amino}furan-2(5H)-one (all known from WO 2007/115644), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](methyl)amino}furan-2(5H)-one, 4-{[(6-chloro-5-fluoropyrid-3-yl)methyl](cyclopropyl)amino}furan-2(5H)-one (both from WO 2007/115643), 4-{[(6-chloropyrid-3-yl)methyl](cyclopropyl)amino}furan-2(5H)-one, 4-{[(6-chloropyrid-3-yl)methyl](methyl)amino}furan-2(5H)-one (both from EP-A-0 539 588), [(6-chloropyridin-3-yl)methyl](methyl)oxido-$\lambda^4$-sulfanylidene cyanamide, [1-(6-chloropyridin-3-yl)ethyl](methyl)oxido-$\lambda^4$-sulfanylidene cyanamide (both from WO 2007/149134) and its diastereomeres (A) and (B)

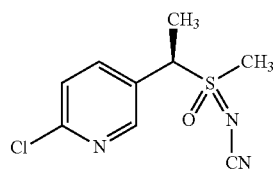

(A)

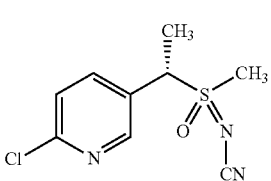
(B)

(also known from WO 2007/149134), [(6-trifluoromethylpyridin-3-yl)methyl](methyl)oxido-λ⁴-sulfanylidene cyanamide (known from WO 2007/095229), or [1-(6-trifluoromethylpyridin-3-yl)ethyl](methyl)oxido-λ⁴-sulfanylidene cyanamide (known from WO 2007/149134) and its diastereomeres (C) and (D), namely Sulfoxaflor (also known from WO 2007/149134)

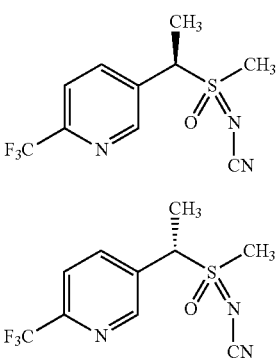
(C)

(D)

Examples of molluscicides which may be mentioned are metaldehyde and methiocarb.

Examples of safeners which may be mentioned are:
(1) Heterocyclic carboxylic acid derivates, for example dichlorophenylpyrazolin-3-carboxylic acid derivatives, e.g. 1-(2,4-dichlorophenyl)-5-(ethoxycarbonyl)-5-methyl-4,5-dihydro-1H-pyrazole-3-carboxylic acid, diethyl 1-(2,4-dichlorophenyl)-4,5-dihydro-5-methyl-1H-pyrazole-3,5-dicarboxylate ("mefenpyr-diethyl"), and similar compounds known from WO 91/07874; for example dichlorophenylpyrazolecarboxylic acid derivatives, e.g. ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 5-tert-butyl-1-(2,4-dichlorophenyl)-1H-pyrazole-3-carboxylate and similar compounds known from EP-A 0 333 131 and EP-A 0 269 806; for example 1,5-diphenylpyrazole-3-carboxylic acid derivatives, e.g. ethyl 1-(2,4-dichlorophenyl)-5-phenyl-1H-pyrazole-3-carboxylate, methyl 1-(2-chlorophenyl)-5-phenyl-1H-pyrazole-3-carboxylate, and similar compounds known from EP-A 0 268 554; for example triazolecarboxylic acid derivatives, e.g. fenchlorazole, fenchlorazole-ethyl, and similar compounds known from EP-A 0 174 562 and EP-A 0 346 620; for example 2-isoxazoline-3-carboxylic acid derivatives, e.g. ethyl 5-(2,4-dichlorobenzyl)-4,5-dihydro-1,2-oxazole-3-carboxylate, ethyl 5-phenyl-4,5-dihydro-1,2-oxazole-3-carboxylate and similar compounds known from WO 91/08202, or 5,5-diphenyl-4,5-dihydro-1,2-oxazole-3-carboxylic acid, ethyl 5,5-diphenyl-4,5-dihydro-1,2-oxazole-3-carboxylate ("isoxadifen-ethyl"), propyl 5,5-diphenyl-4,5-dihydro-1,2-oxazole-3-carboxylate, ethyl 5-(4-fluorophenyl)-5-phenyl-4,5-dihydro-1,2-oxazole-3-carboxylate known from WO 95/07897.

(2) Derivatives of 8-quinolinol, for example derivatives of (quinolin-8-yloxy)acetic acid, e.g. heptan-2-yl[(5-chloroquinolin-8-yl)oxy]acetate ("cloquintocet-mexyl"), 4-methylpentan-2-yl[(5-chloroquinolin-8-yl)oxy]acetate, 4-(allyloxy)butyl[(5-chloroquinolin-8-yl)oxy]acetate, 1-(allyloxy)propan-2-yl[(5-chloroquinolin-8-yl)oxy]acetate, ethyl [(5-chloroquinolin-8-yl)oxy]acetate, methyl [(5-chloroquinolin-8-yl)oxy]acetate, allyl [(5-chloroquinolin-8-yl)oxy]acetate, 2-{[propylideneamino]oxy}ethyl [(5-chloroquinolin-8yl)oxy]acetate, 2-oxopropyl[(5-chloroquinolin-8-yl)oxy]acetate, and similar compounds known from EP-A 0 086 750, EP-A 0 094 349, EP-A 0 191 736 or EP-A 0 492 366, as well as [(5-chloroquinolin-8-yl)oxy]acetic acid, its hydrates and salts, e.g. the lithium, sodium, potassium, calcium, magnesium, aluminum, iron, ammonium, quartanary ammonium, sulfonium or phosphonium salts as known from WO 02/34048; for example derivatives of [(5-chloroquinolin-8-yl)oxy]malonic acid, e.g diethyl [(5-chloroquinolin-8-yl)oxy]malonate, diallyl [(5-chloroquinolin-8-yl)oxy]malonate, ethyl methyl [(5-chloroquinolin-8-yl)oxy]malonate, and similar compounds known from EP-A 0 582 198.

(3) Dichloroacetamides, which are often used as pre-emergence safeners (soil active safeners), e.g. "dichlormid" (N,N-diallyl-2,2-dichloroacetamide), "R-29148" (3 dichloroacetyl-2,2,5-trimethyl-1,3-oxazolidine) and "R-28725" (3-dichloroacetyl-2,2,-dimethyl-1,3-oxazolidine) both of the company Stauffer, "benoxacor" (4-dichloroacetyl-3,4-dihydro-3-methyl-2H-1,4-benzoxazine), "PPG-1292" (N-allyl-N-[(1,3-dioxolan-2-yl)-methyl]-dichloroacetamide) of PPG Industries, "DKA-24" (N-allyl-N-[allylaminocarbonyl)methyl]-dichloroacetamide) of Sagro-Chem, "AD-67" or "MON 4660" (3-dichloroacetyl-1-oxa-3-aza-spiro[4,5]decane) of Nitrokemia and Monsanto, "TI-35" (1-dichloroacetyl-azepane) of TRI-Chemical RT, "diclonon" (dicyclonon) or "BAS145138" or "LAB145138" (3-dichloroacetyl-2,5,5-trimethyl-1,3-diazabicyclo[4.3.0]nonane) of BASF, "Furilazol" or "MON 13900" [(RS)-3-dichloroacetyl-5-(2-furyl)-2,2-dimethyloxazolidine], as well as there (R)-isomer.

(4) Acylsulfonamides, for example N-acylsulfonamide of the formula (II)

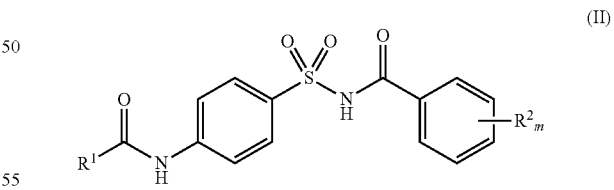
(II)

or its salts (known from WO 97/45016), wherein
R¹ represents $(C_1-C_6)$alkyl, which is unsubstituted or mono- to trisubstituted by substituents selected from the group consisting of halogen, $(C_1-C_4)$alkoxy, $(C_1-C_6)$haloalkoxy and $(C_1-C_4)$alkylthio;
R² represents halogen, $(C_1-C_4)$alkyl, $(C_1-C_4)$alkoxy, $CF_3$;
m is 1 or 2;

or for example 4-(benzoylsulfamoyl)benzamides of the formula (III)

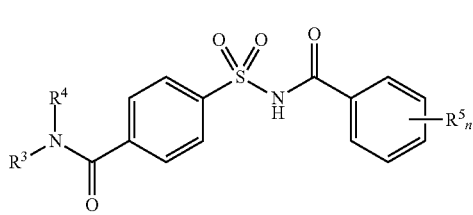

(III)

or its salts (known from WO 99/16744), wherein
$R^3$, $R^4$ independently of one another represent hydrogen, $(C_1-C_6)$alkyl, $(C_3-C_6)$alkenyl, $(C_3-C_6)$alkynyl, $(C_3-C_6)$cycloalkyl,
$R^5$ represents halogen, $(C_1-C_4)$alkyl, $(C_1-C_4)$haloalkyl or $(C_1-C_4)$alkoxy
n is 1 or 2,
in particular compounds of formula (III), wherein
$R^3$=cyclopropyl, $R^4$=hydrogen and $R^5_n$=2-OMe, ("cyprosulfamide"),
$R^3$=cyclopropyl, $R^4$=hydrogen and $R^5_n$=5-Cl-2-OMe,
$R^3$=ethyl, $R^4$=hydrogen and $R^5_n$=2-OMe,
$R^3$=isopropyl, $R^4$=hydrogen and $R^5_n$=5-Cl-2-OMe,
$R^3$=isopropyl, $R^4$=hydrogen and $R^5_n$=2-OMe.
or for example benzoylsulfamoylphenylureas of the formula (IV)

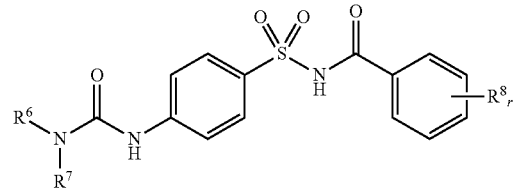

(IV)

(known from EP-A 0 365 484), wherein
$R^6$, $R^7$ independently of one another represent hydrogen, $(C_1-C_8)$alkyl, $(C_3-C_6)$alkenyl, $(C_3-C_6)$alkynyl,
$R^8$ represents halogen, $(C_1-C_4)$alkyl, $(C_1-C_4)$alkoxy, $CF_3$
r is 1 or 2;
in particular
1-[4-($N^2$-methoxybenzoylsulfamoyl)phenyl]-3-methyl urea,
1-[4-($N^2$-methoxybenzoylsulfamoyl)phenyl]-3,3-dimethyl urea,
1-[4-(N-4,5-dimethylbenzoylsulfamoyl)phenyl]-3-methyl urea.
(5) Hydroxyaromatic compounds and aromatic-aliphatic carboxylic acid derivatives, e.g. ethyl 3,4,5-triacetoxybenzoate, 4-hydroxy-3,5-dimethoxybenzoic acid, 3,5-dihydroxybenzoic acid, 2,4-dihydroxybenzoic acid, 4-fluoro-2-hydroxybenzoic acid, 2-hydroxycinnamic acid, 2,4-dichlorocinnamic acid (cf. WO 2004/084631, WO 2005/015994, WO 2005/016001).
(6) 1,2-Dihydrochinoxalin-2-ones, e.g. 1-methyl-3-(2-thienyl)-1,2-dihydrochinoxalin-2-one, 1-methyl-3-(2-thienyl)-1,2-dihydrochinoxalin-2-thione, 1-(2-aminoethyl)-3-(2-thienyl)-1,2-dihydrochinoxalin-2-one hydrochlorid, 1-(2-methylsulfonylaminoethyl)-3-(2-thienyl)-1,2-dihydrochinoxalin-2-one (cf. WO 2005/112630).
(7) Diphenylmethoxyacetic acid derivatives, e.g. methyl (diphenylmethoxy)acetate (CAS-Reg. No. 41858-19-9), ethyl (diphenylmethoxy)acetate or (diphenylmethoxy)acetic acid (cf. WO 98/38856).

(8) Compounds of formula (V)

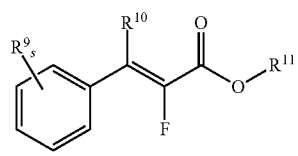

(V)

or its salts (known from WO 98/27049), wherein
$R^9$ represents halogen, $(C_1-C_4)$alkyl, $(C_1-C_4)$haloalkyl, $(C_1-C_4)$alkoxy, $(C_1-C_4)$haloalkoxy,
$R^{10}$ represents hydrogen or $(C_1-C_4)$alkyl,
$R^{11}$ represents hydrogen, in each case unsubstituted or mono- to trisubstituted $(C_1-C_8)$alkyl, $(C_2-C_4)$alkenyl, $(C_2-C_4)$alkynyl, or aryl, where the substituents are selected from the group consisting of halogen and $(C_1-C_8)$alkoxy,
s is 0, 1 or 2.
(9) 3-(5-Tetrazolylcarbonyl)-2-chinolones, e.g. 1,2-dihydro-4-hydroxy-1-ethyl-3-(5-tetrazolylcarbonyl)-2-chinolone (CAS-Reg. No. 219479-18-2), 1,2-dihydro-4-hydroxy-1-methyl-3-(5-tetrazolyl-carbonyl)-2-chinolone (CAS-Reg. No. 95855-00-8) (cf. WO 99/00020).
(10) Compounds of the formulae (VI-a) and (VI-b)

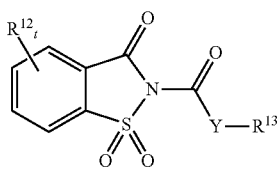

(VI-a)

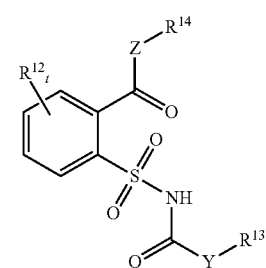

(VI-b)

(known from WO 2007/023719 and WO 2007/023764), wherein
$R^{12}$ represents halogen, $(C_1-C_4)$alkyl, methoxy, nitro, cyano, $CF_3$, $OCF_3$,
Y, Z independently represent O or S,
t is 0, 1, 2, 3 or 4,
$R^{13}$ represents $(C_1-C_{16})$alkyl, $(C_2-C_6)$alkenyl, aryl, benzyl, halogenobenzyl,
$R^{14}$ represents hydrogen or $(C_1-C_6)$alkyl.
(11) Oxyimino compounds, known as seed treatment agents, e.g. "oxabetrinil" [(Z)-1,3-dioxolan-2-ylmethoxyimino(phenyl)acetonitril], "fluxofenim" [1-(4-chlorophenyl)-2,2,2-trifluoro-1-ethanone-O-(1,3-dioxolan-2-ylmethyl)-oxime], and "cyometrinil" or "CGA-43089" [(Z)-cyanomethoxyimino (phenyl)acetonitril], all known as seed treatment safener for sorghum against damage by metolachlor.
(12) Isothiochromanones, e.g. methyl [(3-oxo-1H-2-benzothiopyran-4(3H)-ylidene)methoxy]acetate (CAS-Reg. No. 205121-04-6) and similar compounds known from WO 98/13361.

(13) Compounds from the group consisting of "naphthalic anhydrid" (1,8-naphthalinedicarboxylic acid anhydride), which is known as seed treatment safener for corn (maize) against damage by thiocarbamate herbicides, "fenclorim" (4,6-dichloro-2-phenylpyrimidine), which is known as seed treatment safener in sown rice against damage by pretilachlor, "flurazole" (benzyl-2-chloro-4-trifluoromethyl-1,3-thiazol-5-carboxylate), which is known as seed treatment safener for sorghum against damage by alachlor and metolachlor, "CL 304415" (CAS-Reg. No. 31541-57-8), (4-carboxy-3,4-dihydro-2H-1-benzopyran-4-acetic acid) of American Cyanamid, which is known as safener for corn (maize) against damage by imidazolinones, "MG 191" (CAS-Reg. No. 96420-72-3) (2-dichloromethyl-2-methyl-1,3-dioxolane) of Nitrokemia, known as safener for corn (maize), "MG-838" (CAS-Reg. No. 133993-74-5), (2-propenyl 1-oxa-4-azaspiro[4.5]decane-4-carbodithioate) of Nitrokemia, "Disulfoton" (O,O-diethyl-S-2-ethylthioethyl phosphorodithioate), "dietholate" (O,O-diethyl-O-phenylphosphorothioate), "mephenate" (4-chlorophenyl-methylcarbamate).

(14) Compounds, which besides herbicidal activity als exhibit Safener activity in crops like rice, e.g. "Dimepiperate" or "MY-93" (S-1-methyl-1-phenylethyl-piperidin-1-carbothioate), which is known as safener for rice against damage by molinate, "daimuron" or "SK 23" [1-(1-methyl-1-phenylethyl)-3-p-tolyl-urea], which is known as safener for rice against damage by imazosulfuron, "cumyluron"="JC-940" [3-(2-chlorophenylmethyl)-1-(1-methyl-1-phenyl-ethyl) urea] (cf. JP-A 60-087254), which is known as safener for rice against damage by some herbicides, "methoxyphenon" or "NK 049" (3,3'-dimethyl-4-methoxy-benzophenone), which is known as safener for rice against damage by some herbicides, "CSB" [1-bromo-4-(chloromethylsulfonyl)benzene] of Kumiai (CAS-Reg. No. 54091-06-4), which is known as safener for rice against damage by some herbicides.

(15) Compounds, which are mainly used as herbicides, but which exhibit also safener activity on some crops, e.g. (2,4-dichlorophenoxy)acetic acid (2,4-D), (4-chlorophenoxy)acetic acid, (R,S)-2-(4-chlor-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl-3,6-dichloro-2-methoxybenzoate (lactidichlorethyl).

Examples of plant growth regulators which may be mentioned are chlorocholine chloride and ethephon.

Examples of plant nutrients which may be mentioned are customary inorganic or organic fertilizers for supplying plants with macro- and/or micronutrients.

Suitable exterrnders and/or surfactants which may be contained in the compositions according to the invention are all formulation auxiliaries which can customarily be used in plant treatment compositions.

In the compositions according to the invention the ratio of Propineb to an agrochemically active compound of group (B) can be varied within a relatively wide range. In general, between 0.02 and 2.0 parts by weight, preferably between 0.05 and 1.0 part by weight, of Propineb of the formula (I) is/are employed per part by weight of agrochemically active compound.

When employing the active compounds of the formula (I) which can be used according to the invention as bird repellents, the application rates can be varied within a certain range, depending on the type of application. In the treatment of seed, the application rates of active compound of the formula (I) are generally between 10 and 10000 mg per kilogram of seed, preferably between 10 and 300 mg per kilogram of seed. When used in solid formulations, the application rates of active compound of the formula (I) are generally between 20 and 800 mg per kilogram of formulation, preferably between 30 and 700 mg per kilogram of formulation.

Furthermore the invention relates to a method of repelling birds, characterized in that Propineb is offered to the birds and/or their habitat.

The fungicides used according to the invention are generally applied in form of a composition comprising at least Propineb as mentioned above. Preferably the fungicidal composition comprises agriculturally acceptable additives, solvents, carriers, surfactants, or extenders.

The present invention furthermore relates to compositions comprising the active compound combinations according to the invention. Preferably, the compositions are fungicidal compositions comprising agriculturally suitable carriers or extenders.

According to the invention, carrier is to be understood as meaning a natural or synthetic, organic or inorganic substance which is mixed or combined with the active compounds for better applicability, in particular for application to plants or plant parts or seeds. The carrier, which may be solid or liquid, is generally inert and should be suitable for use in agriculture.

Suitable solid carriers are: for example ammonium salts and natural ground minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral oils and vegetable oils, and also derivatives thereof. It is also possible to use mixtures of such carriers. Solid carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks. Suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, and also protein hydrolysates. Suitable dispersants are: for example lignosulphite waste liquors and methylcellulose.

Suitable liquefied gaseous extenders or carriers are liquids which are gaseous at ambient temperature and under atmospheric pressure, for example aerosol propellants, such as butane, propane, nitrogen and carbon dioxide.

Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils.

If the extender used is water, it is also possible for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

The compositions according to the invention may comprise additional further components, such as, for example, surfactants. Suitable surfactants are emulsifiers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

In general, the compositions according to the invention comprise between 0.05 and 99 percent by weight of the active compound combination according to the invention, preferably between 10 and 70 percent by weight, particularly preferably between 20 and 50 percent by weight, most preferably 25 percent by weight.

The active compound combinations or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flow-able concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also micro-encapsulations in polymeric substances and in coating materials for seed, and also ULV cold-fogging and warm-fogging formulations.

The formulations mentioned can be prepared in a manner known per se, for example by mixing the active compounds or the active compound combinations with at least one additive. Suitable additives are all customary formulation auxiliaries, such as, for example, organic solvents, extenders, solvents or diluents, solid carriers and fillers, surfactants (such as adjuvants, emulsifiers, dispersants, protective colloids, wetting agents and tackifiers), dispersants and/or binders or fixatives, preservatives, dyes and pigments, defoamers, inorganic and organic thickeners, water repellents, if appropriate siccatives and UV stabilizers, gibberellins and also water and further processing auxiliaries. Depending on the formulation type to be prepared in each case, further processing steps such as, for example, wet grinding, dry grinding or granulation may be required.

Organic diluents that may be present are all polar and non-polar organic solvents that are customarily used for such purposes. Preferred are ketones, such as methyl isobutyl ketone and cyclohexanone, furthermore amides, such as dimethylformamide and alkanecarboxamides, such as N,N-dimethyldecanamide and N,N-dimethyloctanamide, furthermore cyclic compounds, such as N-methylpyrrolidone, N-octylpyrrolidone, N-dodecylpyrrolidone, N-octylcaprolactam, N-dodecylcaprolactam and butyrolactone, additionally strongly polar solvents, such as dimethyl sulphoxide, furthermore aromatic hydrocarbons, such as xylene, Solvesso™, mineral oils, such as white spirit, petroleum, alkylbenzenes and spindle oil, moreover esters, such as propylene glycol monomethyl ether acetate, dibutyl adipate, hexyl acetate, heptyl acetate, tri-n-butyl citrate and di-n-butyl phthalate, and furthermore alcohols, such as, for example, benzyl alcohol and 1-methoxy-2-propanol.

Solid carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks.

Suitable surfactants (adjuvants, emulsifiers, dispersants, protective colloids, wetting agents and tackifiers) are customary ionic and nonionic substances. Examples which may be mentioned are ethoxylated nonylphenols, polyalkylene glycol ethers of straight-chain or branched alcohols, products of reactions of alkylphenols with ethylene oxide and/or propylene oxide, products of reactions of fatty amines with ethylene oxide and/or propylene oxide, furthermore fatty esters, alkylsulphonates, alkyl sulphates, alkyl ether sulphates, alkyl ether phosphates, aryl sulphates, ethoxylated arylalkylphenols, such as, for example, tristyrylphenol ethoxylates, furthermore ethoxylated and propoxylated arylalkylphenols and also sulphated or phosphated arylalkylphenol ethoxylates or ethoxy- and propoxylates. Mention may furthermore be made of natural and synthetic water-soluble polymers, such as lignosulphonates, gelatine, gum arabic, phospholipids, starch, hydrophobically modified starch and cellulose derivatives, in particular cellulose esters and cellulose ethers, furthermore polyvinyl alcohol, polyvinyl acetate, polyvinylpyrrolidone, polyacrylic acid, polymethacrylic acid and copolymers of (meth)acrylic acid and (meth)acrylic acid esters, and moreover also alkali metal hydroxide-neutralized copolymers of methacrylic acid and methacrylic ester and condensates of optionally substituted naphthalenesulphonic acid salts with formaldehyde.

Suitable solid fillers and carriers are all substances customarily used for this purpose in crop pretection compositions. Inorganic particles, such as carbonates, silicates, sulphates and oxides having a mean particle size of from 0.005 to 20 µm, particularly preferably from 0.02 to 10 µm, may be mentioned as being preferred. Examples which may be mentioned are ammonium sulphate, ammonium phosphate, urea, calcium carbonate, calcium sulphate, magnesium sulphate, magnesium oxide, aluminium oxide, silicon dioxide, finely divided silicic acid, silica gels, natural and synthetic silicates and alumosilicates and vegetable products such as cereal meal, wood powder and cellulose powder.

Suitable colorants that may be present in the seed dressing formulations to be used according to the invention include all colorants customary for such purposes. Use may be made both of pigments, of sparing solubility in water, and of dyes, which are soluble in water. Examples that may be mentioned include the colorants known under the designations Rhodamin B, C.I. Pigment Red 112 and C.I. Solvent Red 1. The colorants used can be inorganic pigments, for example iron oxide, titanium oxide, Prussian Blue, and organic dyes, such as alizarin, azo and metal phthalocyanine dyes, and trace nutrients, such as salts of iron, manganese, boron, copper, cobalt, molybdenum and zinc.

Suitable wetting agents that may be present in the seed dressing formulations to be used according to the invention include all substances which promote wetting and are customary in the formulation of agrochemically active compounds. Preference is given to using alkylnaphthalenesulphonates, such as diisopropyl- or diisobutylnaphthalenesulphonates.

Suitable dispersants and/or emulsifiers that may be present in the seed dressing formulations to be used according to the invention include all nonionic, anionic and cationic dispersants which are customary in the formulation of agrochemically active compounds. Preference is given to using nonionic or anionic dispersants or mixtures of nonionic or anionic dispersants. Particularly suitable nonionic dispersants are ethylene oxide/propylene oxide block polymers, alkylphenol polyglycol ethers, and also tristryrylphenol polyglycol ethers and their phosphated or sulphated derivatives. Particularly suitable anionic dispersants are lignosulphonates, polyacrylic acid salts and arylsulphonate/formaldehyde condensates.

Defoamers that may be present in the seed dressing formulations to be used according to the invention include all foam-inhibiting compounds which are customary in the formulation of agrochemically active compounds. Preference is given to using silicone defoamers, magnesium stearate, silicone emulsions, long-chain alcohols, fatty acids and their salts and also or -ganofluorine compounds and mixtures thereof.

Preservatives that may be present in the seed dressing formulations to be used according to the invention include all compounds which can be used for such purposes in agrochemical compositions. By way of example, mention may be made of dichlorophen and benzyl alcohol hemiformal.

Secondary thickeners that may be present in the seed dressing formulations to be used according to the invention include all compounds which can be used for such purposes in agrochemical compositions. Preference is given to cellulose derivatives, acrylic acid derivatives, polysaccharides, such as xanthan gum or Veegum, modified clays, phyllosilicates, such as attapulgite and bentonite, and also finely divided silicic acids.

Suitable adhesives that may be present in the seed dressing formulations to be used according to the invention include all customary binders which can be used in seed dressings. Polyvinylpyrrolidone, polyvinyl acetate, polyvinyl alcohol and tylose may be mentioned as being preferred.

Suitable gibberellins that may be present in the seed dressing formulations to be used according to the invention are preferably the gibberellins A1, A3 (=gibberellic acid), A4 and A7; particular preference is given to using gibberellic acid. The gibberellins are known (cf. R. Wegler "Chemie der Pflanzenschutz- and Schadlingsbekampfungsmittel" [Chemistry of Crop Protection Agents and Pesticides], Vol. 2, Springer Verlag, 1970, pp. 401-412).

The formulations generally comprise between 0.1 and 95% by weight of active compound, preferably between 0.5 and 90%.

The active compound combinations according to the invention can be present in commercial formulations and in the use forms prepared from these formulations as a mixture with other active compounds, such as insecticides, attractants, sterilants, bactericides, acaricides, nematicides, fungicides, growth regulators or herbicides. A mixture with fertilizers is also possible.

The treatment according to the invention of the plants and plant parts with the active compound combinations or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. Preference is given to application by dipping, spraying, atomizing, irrigating, evaporating, dusting, fogging, broadcasting, foaming, painting, spreading-on, watering (drenching) and drip irrigating.

The application of the formulations is carried out in accordance with customary agricultural practice in a manner adapted to the application forms. Customary applications are, for example, dilution with water and spraying of the resulting spray liquor, application after dilution with oil, direct application without dilution, seed dressing or soil application of carrier granules.

The active compound content of the application forms prepared from the commercial formulations can vary within wide limits. The active compound concentration of the application forms can be from 0.0000001 up to 95% by weight of active compound, preferably between 0.0001 and 2% by weight.

The compositions according to the invention do not only comprise ready-to-use compositions which can be applied with suitable apparatus to the plant or the seed, but also commercial concentrates which have to be diluted with water prior to use.

The active compound combinations or compositions according to the invention have strong microbicidal activity and can be used for controlling unwanted microorganisms, such as fungi and bacteria, in crop protection.

In crop protection, fungicides can be used for controlling Plasmodiophoromycetes, Oomycetes, Chytridiomycetes, Zygomycetes, Ascomycetes, Basidiomycetes and Deuteromycetes.

In crop protection, bactericides can be used for controlling Pseudomonadaceae, Rhi-zobiaceae, Enterobacteriaceae, Corynebacteriaceae and Streptomycetaceae.

The fungicidal compositions according to the invention can be used for the curative or protective control of phytopathogenic fungi. Accordingly, the invention also relates to curative and protective methods for controlling phytopathogenic fungi using the active compound combinations or compositions according to the invention, which are applied to the seed, the plant or plant parts, the fruit or the soil in which the plants grow. Preference is given to application onto the plant or the plant parts, the fruits or the soil in which the plants grow.

According to the invention, it is possible to treat all plants and parts of plants. Plants are to be understood here as meaning all plants and plant populations, such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by varietal property rights. Parts of plants are to be understood as meaning all above-ground and below-ground parts and organs of the plants, such as shoot, leaf, flower and root, examples which may be mentioned being leaves, needles, stems, trunks, flowers, fruit bodies, fruits and seeds and also roots, tubers and rhizomes. Plant parts also include harvested material and vegetative and generative propagation material, for example seedlings, tubers, rhizomes, cuttings and seeds. Preference is given to the treatment of the plants and the above-ground and below-ground parts and organs of the plants, such as shoot, leaf, flower and root, examples which may be mentioned being leaves, needles, stems, trunks, flowers, fruits.

The following plants may be mentioned as plants which can be treated according to the invention: cotton, flax, grapevines, fruit, vegetable, such as *Rosaceae* sp. (for example pomaceous fruit, such as apples and pears, but also stone fruit, such as apricots, cherries, almonds and peaches and soft fruit such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit), *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumbers), *Alliaceae* sp. (for example leek, onions), *Papilionaceae* sp. (for example peas); major crop plants, such *Gramineae* sp. (for example maize, lawn, cereals such as wheat, rye, rice, barley, oats, millet and triticale), *Asteraceae* sp. (for example sunflowers), *Brassicaceae* sp. (for example white cabbage, red cabbage, broccoli, cauliflowers, brussel sprouts, pak Choi, kohlrabi, garden radish, and also oilseed rape, mustard, horseradish and cress), *Fabacae* sp. (for example beans, peas), *Papilionaceae* sp. (for example soya beans), *Solanaceae* sp. (for example potatoes), *Chenopodiaceae* sp. (for example sugarbeet, fodderbeet, swiss chard, beetroot); crop plants and ornamental plants in garden and forest; and also in each case genetically modified varieties of these plants. Preferably, cereals, maize, sunflower, soya beans are treated according to the invention.

The method according to the invention for controlling phytopathogenic fungi can also be employed for treating genetically modified organisms, for example plants or seeds. Genetically modified plants are plants whose genome has, stably integrated, a certain heterologous gene coding for a certain protein. Here, "heterologous gene" is meant to be understood as a gene which confers novel agronomical properties on the transformed plant, or a gene which improves the agronomical quality of the modified plant.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The terms "parts", "parts of plants" and "plant parts" have been explained above. Particularly preferably, plants of the plant cultivars which are in each case commercially available or in use are treated according to the invention.

Depending on the plant species or plant cultivars, their location and growth conditions (soil, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of trans-genic plants which may be mentioned are the important crop plants, such as cereals (wheat, rice), maize, soya beans, potatoes, cotton, oilseed rape, and also fruit plants (with the fruits apples, pears, citrus fruits and grapes), and particular emphasis is given to maize, soya beans, potatoes, cotton, and oilseed rape. "Traits" that are emphasized are in particular increased defence of the plants against insects by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), Knock-Out® (for example maize), StarLink® (for example maize), Bollgard® (cotton), Nucotn® (cotton) and NewLeaf® (potatoes). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

A further application of the active compound combinations and compositions according to the invention is the protection of wood and timber. The insecticidal and fungicidal compositions or concentrates used for protecting wood and timber comprise the active compound according to the invention in a concentration of from 0.0001 to 95% by weight, in particular from 0.001 to 60% by weight.

Some pathogens of fungal diseases which can be treated according to the invention may be mentioned by way of example, but not by way of limitation:

Diseases caused by powdery mildew pathogens, such as, for example, *Blumeria* species, such as, for example, *Blumeria graminis*; *Podosphaera* species, such as, for example, *Podosphaera leucotricha*; *Sphaerotheca* species, such as, for example, *Sphaerotheca fuliginea*; *Uncinula* species, such as, for example, *Uncinula necator*;

Diseases caused by rust disease pathogens, such as, for example, *Gymnosporangium* species, such as, for example, *Gymnosporangium sabinae*; *Hemileia* species, such as, for example, *Hemileia vastatrix*; *Phakopsora* species, such as, for example, *Phakopsora pachyrhizi* and *Phakopsora meibomiae*; *Puccinia* species, such as, for example, *Puccinia recondita* or *Puccinia triticina*; *Uromyces* species, such as, for example, *Uromyces appendiculatus*;

Diseases caused by pathogens from the group of the Oomycetes, such as, for example, *Bremia* species, such as, for example, *Bremia lactucae*; *Peronospora* species, such as, for example, *Peronospora pisi* or *P. brassicae*; *Phytophthora* species, such as, for example *Phytophthora infestans*; *Plasmopara* species, such as, for example, *Plasmopara viticola*; *Pseudoperonospora* species, such as, for example, *Pseudoperonospora humuli* or *Pseudoperonospora cubensis*; *Pythium* species, such as, for example, *Pythium ultimum*;

Leaf blotch diseases and leaf wilt diseases caused, for example, by *Alternaria* species, such as, for example, *Alternaria solani*; *Cercospora* species, such as, for example, *Cercospora beticola*; *Cladiosporium* species, such as, for example, *Cladiosporium cucumerinum*; *Cochliobolus* species, such as, for example, *Cochliobolus sativus* (conidia form: *Drechslera*, Syn: *Helminthosporium*); *Colletotrichum* species, such as, for example, *Colletotrichum lindemuthanium*; *Cycloconium* species, such as, for example, *Cycloconium oleaginum*; *Diaporthe* species, such as, for example, *Diaporthe citri*; *Elsinoe* species, such as, for example, *Elsinoe fawcettii*; *Gloeosporium* species, such as, for example, *Gloeosporium laeticolor*; *Glomerella* species, such as, for example, *Glomerella cingulata*; *Guignardia* species, such as, for example, *Guignardia bidwelli*; *Leptosphaeria* species, such as, for example, *Leptosphaeria maculans*; *Magnaporthe* species, such as, for example, *Magnaporthe grisea*; *Microdochium* species, such as, for example, *Microdochium nivale*; *Mycosphaerella* species, such as, for example, *Mycosphaerella graminicola* and *M. fijiensis*; *Phaeosphaeria* species, such as, for example, *Phaeosphaeria nodorum*; *Pyrenophora* species, such as, for example, *Pyrenophora teres*; *Ramularia* species, such as, for example, *Ramularia* collo-cygni; *Rhynchosporium* species, such as, for example, *Rhynchosporium secalis*; *Septoria* species, such as, for example, *Septoria apii*; *Typhula* species, such as, for example, *Typhula incarnata*; *Venturia* species, such as, for example, *Venturia inaequalis*;

Root and stem diseases caused, for example, by *Corticium* species, such as, for example, *Corticium graminearum*; *Fusarium* species, such as, for example, *Fusarium oxysporum*; *Gaeumannomyces* species, such as, for example, *Gaeumannomyces graminis*; *Rhizoctonia* species, such as, for example *Rhizoctonia solani*; *Tapesia* species, such as, for example, *Tapesia acuformis*; *Thielaviopsis* species, such as, for example, *Thielaviopsis basicola*;

Ear and panicle diseases (including maize cobs) caused, for example, by *Alternaria* species, such as, for example, *Alternaria* spp.; *Aspergillus* species, such as, for example, *Aspergillus flavus*; *Cladosporium* species, such as, for example, *Cladosporium cladosporioides*; *Claviceps* species, such as, for example, *Claviceps purpurea*; *Fusarium* species, such as, for example, *Fusarium culmorum*; *Gibberella* species, such as, for example, *Gibberella zeae*; *Monographella* species, such as, for example, *Monographella nivalis*; *Septoria* species, such as for example, *Septoria nodorum*;

Diseases caused by smut fungi, such as, for example, *Sphacelotheca* species, such as, for example, *Sphacelotheca reiliana*; *Tilletia* species, such as, for example, *Tilletia caries*; *T. controversa*; *Urocystis* species, such as, for example, *Urocystis occulta*; *Ustilago* species, such as, for example, *Ustilago nuda*; *U. nuda tritici*;

Seed- and soil-borne rot and wilt diseases, and also diseases of seedlings, caused, for example, by *Fusarium* species, such as, for example, *Fusarium culmorum*; *Microdochium* species, such as, for example, *Microdochium nivale*; *Tilletia* species, such as, for example, *Tilletia caries*; *Ustilago* species, such as, for example, *Ustilago tritici*, *Utilago nuda*; *Pyrenophora* species, such as, for example, *Pyrenophora graminea, Prenophora teres*; *Phytophthora* species, such as, for example, *Phytophthora cactorum*; *Pythium* species, such as, for example, *Pythium ultimum*; *Rhizoctonia* species, such as, for example, *Rhizoctonia solani*; *Sclerotium* species, such as, for example, *Sclerotium rolfsii*; *Alternaria* species, such as, for example, *Alternaria brassicae*; *Phoma* species, such as, for example, *Phoma lingam*.

Diseases of flowers and seeds caused, for example, by *Botrytis* species, such as, for example, *Botrytis cinerea*;

Diseases of plant tubers caused, for example, by *Rhizoctonia* species, such as, for example, *Rhizoctonia solani*; *Helminthosporium* species, such as, for example, *Helminthosporium solani*;

Diseases caused by bacteriopathogens, such as, for example, *Xanthomonas* species, such as, for example, *Xanthomonas campestris* pv. oryzae; *Pseudomonas* species, such as, for example, *Pseudomonas syringae* pv. lachrymans; *Erwinia* species, such as, for example, *Erwinia amylovora*.

Preference is given to controlling the following:

Seed- and soil-borne rot and wilt diseases, and also diseases of seedlings, caused, for example, by *Fusarium* species, such as, for example, *Fusarium culmorum*; *Microdochium* species, such as, for example, *Microdochium nivale*; *Tilletia* species, such as, for example, *Tilletia caries*; *Ustilago* species, such as, for example, *Ustilago tritici, Ustilago nuda*; *Pyrenophora* species, such as, for example, *Pyrenophora graminea, Pyrenophora teres*; *Phytophthora* species, such as, for example, *Phytophthora cactorum*; *Pythium* species, such as, for example, *Pythium ultimum*; *Rhizoctonia* species, such as, for example, *Rhizoctonia solani*; *Sclerotium* species, such as, for example, *Sclerotium rolfsii*; *Alternaria* species, such as, for example, *Alternaria brassicae*; *Phoma* species, such as, for example, *Phoma lingam*.

It is also possible to control resistant strains of the organisms mentioned above.

The application rate of the active compound combinations according to the invention is when treating seed: from 2 to 400 g per 100 kg of seed, preferably from 5 to 200 g pro 100 kg of seed, particularly preferably from 10 to 175 g per 100 kg of seed;

These application rates are mentioned only by way of example and not by way of limitation in the sense of the invention.

The active compound combinations or compositions according to the invention can thus be employed for protecting plants for a certain period of time after treatment against attack by the pathogens mentioned. The period for which protection is provided extends generally for 1 to 28 days, preferably 1 to 14 days, after the treatment of the plants with the active compounds, or up to 200 days after a seed treatment.

In addition, by the treatment according to the invention it is possible to reduce the mycotoxin content in the harvested material and the foodstuff and feedstuff prepared therefrom. Particular, but not exclusive, mention may be made here of the following mycotoxins: deoxynivalenol (DON), nivalenol, 15-Ac-DON, 3-Ac-DON, T2- and HT2-toxin, fumonisine, zearalenon, moniliformin, fusarin, diaceotoxyscirpenol (DAS), beauvericin, enniatin, fusaroproliferin, fusarenol, ochratoxins, patulin, ergot alkaloids and aflatoxins produced, for example, by the following fungi: *Fusarium* spec., such as *Fusarium acuminatum, F. avenaceum, F. crookwellense, F culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, inter alia, and also by *Aspergillus* spec., *Penicillium* spec., *Claviceps purpurea, Stachybotrys* spec. inter alia.

The invention furthermore comprises a method for treating seed where the individual active compounds are applied simultaneously to the seed. Moreover, the invention comprises a method for treating seed where the individual active compounds are applied successively to the seed. Moreover, the invention comprises a method for treating seed where an individual active compound is applied first, followed by a binary mixture of the two other active compounds. Alternatively, it is also possible to apply to the seed first a binary mixture, followed by the remaining individual active compound. If active compounds and/or individual active compounds and binary mixtures are applied separately, this is preferably carried out in different layers. These layers may additionally be separated by layers without active compound.

The invention furthermore relates to seed treated according to one of the methods described in the preceding paragraph.

The active compound combinations or compositions according to the invention are especially suitable for treating seed. A large part of the damage to crop plants caused by harmful organisms is triggered by an infection of the seed during storage or after sowing as well as during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of phytopathogenic fungi by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants or which at least considerably reduce additional application. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

Accordingly, the present invention also relates in particular to a method for protecting seed and germinating plants against attack by phytopathogenic fungi by treating the seed with a composition according to the invention. The invention also relates to the use of the compositions according to the invention for treating seed for protecting the seed and the germinating plant against phytopathogenic fungi. Furthermore, the invention relates to seed treated with a composition according to the invention for protection against phytopathogenic fungi.

The control of phytopathogenic fungi which damage plants post-emergence is carried out primarily by treating the soil and the above-ground parts of plants with crop protection compositions. Owing to the concerns regarding a possible impact of the crop protection composition on the environment and the health of humans and animals, there are efforts to reduce the amount of active compounds applied.

One of the advantages of the present invention is that, because of the particular systemic properties of the compositions according to the invention, treatment of the seed with these compositions not only protects the seed itself, but also the resulting plants after emergence, from phytopathogenic fungi. In this manner, the immediate treatment of the crop at the time of sowing or shortly thereafter can be dispensed with.

It is also considered to be advantageous that the mixtures according to the invention can be used in particular also for transgenic seed where the plant growing from this seed is capable of expressing a protein which acts against pests. By treating such seed with the active compound combinations or compositions according to the invention, even by the expression of the, for example, insecticidal protein, certain pests may be controlled. Surprisingly, a further synergistic effect may be observed here, which additionally increases the effectiveness of the protection against attack by pests.

The compositions according to the invention are suitable for protecting seed of any plant variety employed in agriculture. In particular, this takes the form of seed of maize, peanuts, oilseed rape, poppies, soya bean, beets (for example sugar beets and fodder beets), rice, millet, wheat, barley, rye, triticale, oats, cotton, potatoes, sunflowers, beans, vegetables (such as tomatoes, cucumbers, onions and lettuce), and a range of the so-called energy crops such as miscanthus, pennisetum, Sudan grass, white sweet clover.

As already described, the treatment of transgenic seed with the active compound combinations or compositions according to the invention is of particular importance. This refers to the seed of plants containing at least one heterologous gene which allows the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. Particularly preferably, the heterologous gene originates from *Bacillus thuringiensis*.

In the context of the present invention, the active compound combinations or compositions according to the invention are applied on their own or in a suitable formulation to the seed. Preferably, the seed is treated in a state in which it is sufficiently stable so that the treatment does not cause any damage. In general, treatment of the seed may take place at any point in time between harvesting and sowing. Usually, the seed used is separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the compositions to the seed in the form of a suitable formulation. Suitable formulations and methods for the treatment of seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The invention is illustrated by—but not limited to—the examples below.

USE EXAMPLE

Screening Experiment with Pigeon on the Repellency of Maize Seeds Treated with Different Thiram and Propineb Formulations 15 singly housed pigeons were acclimated to maize as food source over a couple of days. From day—3 to day—1 they received exclusively untreated maize (40 g/bird). Food consumption was determined (see Table 1 below). All birds accepted maize seed as food. The different groups behaved similarly:

TABLE 1

| | | Food consumption of untreated maize (in g) between day −3 and day −1 | | | | |
|---|---|---|---|---|---|---|
| Aviary | Group | Day −3 2008 Oct. 26 | Day −2 2008 Oct. 27 | Day −1 2008 Oct. 28 | Mean/ birds | Mean/ group |
| 1 | Thiram | 15.46 | 22.81 | 21.82 | 20.03 | 20.4 |
| 2 | 160 g/dt | 20.93 | 24.49 | 21.01 | 22.14 | |
| 3 | | 14.10 | 20.52 | 22.65 | 19.09 | |
| 4 | Thiram | 12.42 | 18.38 | 18.25 | 16.35 | 18.5 |
| 5 | 80 g/dt | 19.04 | 23.16 | 21.61 | 21.27 | |
| 6 | | 15.20 | 18.25 | 20.30 | 17.92 | |
| 7 | Propineb | 10.83 | 18.02 | 3.50 | 10.78 | 10.1 |
| 8 | 160 g/dt | 5.02 | 16.62 | 12.45 | 11.36 | |
| 9 | | 3.88 | 16.14 | 4.68 | 8.23 | |
| 10 | Propinep | 5.33 | 9.96 | 12.29 | 9.19 | 15.6 |
| 11 | 80 g/dtr | 25.31 | 26.33 | 20.36 | 24.00 | |
| 12 | | 18.72 | 15.47 | 6.44 | 13.54 | |

For 3 days each of the pigeons received 40 untreated and 40 g treated maize. Food was offered in 2 bowls, one with treated, the other with untreated maize. The position of the two bowls was changed from day to day as well as during the day. Food consumption was again measured (see Table 2 below)

Group 1 (Aviary 1 to 3): Thiram 160 g/dt

Group 2 (Aviary 4 to 6): Thiram 80 g/dt

Group 3 (Aviary 7 to 9): Propineb 160 g/dt

Group 4 (Aviary 10 to 12): Propineb 80 g/dt

TABLE 2

| | | Food consumption of untreated and treated maize (in g) | | | | | | | | |
|---|---|---|---|---|---|---|---|---|---|---|
| | | Day 0 2008 Oct. 29 | | Day 1 2008 Oct. 30 | | Day 2 2008 Oct. 31 | | Mean/birds | | Mean/group |
| Aviary | Group | U | T | U | T | U | T | U | T | U | T |
| 1 | Thiram 160 g/dt | 1.4 | 17.4 | 7.2 | 15.8 | 14.5 | 8.4 | 7.7 | 13.9 | 18.6 | 4.6 |
| 2 | | 27.8 | 0.0 | 25.8 | 0.0 | 23.4 | 0.0 | 25.6 | 0.0 | | |
| 3 | | 21.5 | 0.0 | 22.5 | 0.0 | 23.0 | 0.0 | 22.4 | 0.0 | | |
| 4 | Thiram 80 g/dt | 14.4 | 2.8 | 11.8 | 0.6 | 14.5 | 3.2 | 13.6 | 2.2 | 16.8 | 0.7 |
| 5 | | 15.8 | 0.0 | 18.4 | 0.0 | 19.3 | 0.0 | 17.8 | 0.0 | | |
| 6 | | 18.9 | 0.0 | 18.2 | 0.0 | 19.7 | 0.0 | 18.9 | 0.0 | | |
| 7 | Propineb 160 g/dt | 23.1 | 0.0 | 24.6 | 0.0 | 26.1 | 0.0 | 24.6 | 0.0 | 24.4 | 0.2 |
| 8 | | 24.6 | 0.0 | 19.5 | 1.8 | 19.9 | 0.0 | 21.3 | 0.6 | | |
| 9 | | 20.0 | 0.0 | 30.2 | 0.0 | 28.3 | 0.0 | 26.2 | 0.0 | | |
| 10 | Propineb 80 g/dt | 17.1 | 1.3 | 17.5 | 2.9 | 25.9 | 0.0 | 20.1 | 1.4 | 20.6 | 1.7 |
| 11 | | 20.3 | 0.0 | 23.2 | 1.7 | 27.5 | 0.0 | 23.6 | 0.6 | | |
| 12 | | 4.8 | 7.2 | 20.6 | 1.8 | 28.6 | 0.0 | 18.0 | 3.0 | | |

U. untreated; T:. treated

TABLE 3

| | | day 0 | | day 1 | | day 3 | |
|---|---|---|---|---|---|---|---|
| | | untreated | treated | untreated | treated | untreated | treated |
| Group 1 | Thiram 160 g/dt | 16.9 | 6.0 | 18.5 | 5.3 | 20.3 | 2.8 |
| Group 2 | Thiram 80 g/dt | 16.4 | 0.9 | 16.1 | 0.2 | 17.8 | 1.1 |
| Group 3 | Propineb 160 g/dt | 22.6 | 0.0 | 24.8 | 0.6 | 24.8 | 0.0 |
| Group 4 | Propineb 80 g/dt | 14.1 | 2.8 | 20.4 | 2.1 | 27.3 | 0.0 |

From this example, it can be stated that Propineb achieved a substantially better activity than Thiram when compared at the registered rate of Thiram.

The invention claimed is:

1. A Method of repelling a bird comprising offering a composition comprising Propineb to a bird and/or a habitat thereof, wherein said propineb repels a bird.

2. The method of claim 1, wherein said composition comprises
   A) Propineb, and
   B) an agrochemically active compound.

3. The method of claim 2, wherein the ratio of (A) to (B) is between 0.02 and 2.0 parts by weight.

4. The method of claim 2, wherein the ratio of (A) to (B) is between 0.05 and 1.0 parts by weight.

5. The method of claim 1, wherein said composition comprises an inorganic particle having a mean particle size of from 0.005 to 20 µm.

6. The method of claim 1, wherein said composition is applied to a seed or plant.

7. The method of claim 6, wherein said composition is applied to a seed at a rate of from 2 to 400 g per 100 kg of seed.

8. The method of claim 6, wherein said composition is applied to a seed at a rate of from 5 to 200 g per 100 kg of seed.

9. The method of claim 6, wherein said composition is applied to a seed at a rate of from 10 to 175 g per 100 kg of seed.

10. The method of claim 6, wherein said seed is a maize seed.

11. The method of claim 6, wherein said seed is derived from a transgenic plant.

12. The method of claim 6, wherein said composition protects a seed or plant for up to 200 days.

13. The method of claim 2, wherein said agrochemically active compound is selected from the group consisting of a bactericide, fungicide, an insecticide, an acaricide, a nematicide, a molluscicide, a safener, a plant growth regulators, and a plant nutrient an insecticide.

14. A method of protecting a seed or plant from a bird comprising treating said seed or said plant with a composition comprising Propineb, wherein said propineb protects a seed or plant from a bird.

15. The method of claim 14, wherein said composition comprises
    A) Propineb, and
    B) an agrochemically active compound.

16. The method of claim 15, wherein said agrochemically active compound is selected from the group consisting of a bactericide, fungicide, an insecticide, an acaricide, a nematicide, a molluscicide, a safener, a plant growth regulators, and a plant nutrient an insecticide.

17. The method of claim 15, wherein the ratio of (A) to (B) is between 0.02 and 2.0 parts by weight.

18. The method of claim 15, wherein the ratio of (A) to (B) is between 0.05 and 1.0 parts by weight.

19. The method of claim 15, wherein said composition is applied to a seed at a rate of from 2 to 400 g per 100 kg of seed.

20. A Method of repelling a bird comprising offering a composition consisting essentially of Propineb to a bird and/or a habitat thereof, wherein said propineb repels a bird.

* * * * *